United States Patent [19]

Perlman et al.

[11] Patent Number: 4,810,631

[45] Date of Patent: Mar. 7, 1989

[54] SIGNAL ENHANCEMENT IN IMMUNOASSAY BY MODULATION OF CHEMICAL CATALYSIS

[75] Inventors: Michael E. Perlman, Durham, N.C.; Susan A. Evans, Miami, Fla.

[73] Assignee: Becton, Dickinson and Company, Franklin Lakes, N.J.

[21] Appl. No.: 861,818

[22] Filed: May 12, 1986

[51] Int. Cl.$^4$ .................. G01N 33/53; G01N 33/543; G01N 33/542; C12Q 1/44
[52] U.S. Cl. .......................... 435/7; 435/18; 435/19; 435/21; 435/810; 436/518; 436/537; 436/808; 436/821
[58] Field of Search ................. 435/7, 18, 19, 21, 810, 435/175, 183, 184, 176, 177, 181, 195, 212; 436/518, 808, 821, 904, 537

[56] References Cited

U.S. PATENT DOCUMENTS

| | | | |
|---|---|---|---|
| 4,160,645 | 7/1979 | Ullman | 424/12 X |
| 4,233,144 | 11/1980 | Pace et al. | 436/544 |
| 4,375,972 | 3/1983 | Forgione et al. | 436/531 |
| 4,463,090 | 7/1984 | Harris | 435/7 |
| 4,595,655 | 6/1986 | Self | 436/536 X |

OTHER PUBLICATIONS

Milovanovic, G., Microchem Journ., 28:437–457 (1983).
Bontchev, P., Talanta, 19:675 (1972).
Dolmanova, I. et al., J. Anal. Chem. USSR, 32:638 (1977).
Antonov, V., et al., J. Anal. Chem. USSR, 31:168 (1976).

Primary Examiner—Robert J. Warden
Assistant Examiner—Jack Spiegel
Attorney, Agent, or Firm—Richard E. Brown

[57] ABSTRACT

A method for immunoassay for a ligand suspected to be present in a fluid includes use of an enzyme, a metal ion catalyst for an indicator reaction and a blocked modulator for the catalyst. Ligand present in the fluid binds to an antiligand. The resulting bound fraction activates the enzyme to unblock the modulator. The free modulator activates or inhibits the catalyst thereby modulating the rate of an indicator reaction between a substrate and a redox reagent. The presence of absence of the ligand in the fluid is indicated by a signal, such as a color change or a rate of color change, consequent to the indicator reaction. The invention includes a kit of materials useful for performing the method of the invention.

39 Claims, No Drawings

SIGNAL ENHANCEMENT IN IMMUNOASSAY BY MODULATION OF CHEMICAL CATALYSIS

BACKGROUND OF THE INVENTION

1. Field of the Invention

This invention relates to immunoassay of an analyte and materials used therein, and more particularly relates to a method and materials for immunoassay in which enhancement of a detectable signal is achieved by modulation of chemical catalysis of an indicator reaction.

2. Description of the Invention

Assay systems which are both rapid and sensitive have been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer. Immunoassay procedures may be carried out in solution or on a solid support and may be either heterogeneous or homogeneous. Heterogeneous assays require a separation of bound tracer from free (unbound) tracer. Homogeneous assays do not require a separation step and thereby provide significant advantages in speed, convenience and ease of automation over heterogeneous assays.

Radioimmunoassay (RIA) procedures use radioisotopes as labels, provide high levels of sensitivity and reproducibility, and are amenable to automation for rapid processing or large numbers of samples. However, all RIA procedures require a separation step, since the parameter measured (nuclear decay) cannot be controlled by changing assay conditions or components. In addition, isotopes are costly, have relatively short shelf lives, require expensive and complex equipment, and extensive safety measures for their handling and disposal must he followed.

Fluoroimmunoassay (FIA) uses fluorochromes as labels, provides direct detection of the label, and is readily adaptable to homogeneous assay procedures. However, known homogeneous FIA methods using organic fluorochromes, such as fluorescein or rhodamine derivatives, have not achieved the high sensitivity of RIA, largely because of light scattering by impurities suspended in the assay medium and by background fluorescence emission from other fluorescent materials present in the assay medium.

Enzymes have also been used as labels in immunoassay. In conventional enzyme immunoassay (EIA), an enzyme is covalently conjugated with one component of a specifically binding antigen-antibody pair, and the resulting enzyme conjugate is reacted with a substrate to produce a signal which is detected and measured. Detection of the signal with the naked eye is limited because the average individual can detect the presence of chromophores only down to about $10^{-5}$ or $10^{-6}M$, and ligands to be detected or measured in biological fluids are often present in the range of $10^{-9}$ to $10^{-12}M$.

EIA sensitivity can often be increased by spectrophotometric techniques; however, these procedures require expensive equipment. In another approach, the sensitivity is increased by cascade amplification. In this procedure, the number of detectable (generally colored) molecules is increased by use of two or more enzymes or enzyme derivatives in which a first enzyme conjugated to an assay ligand activates a second enzyme or enzyme derivative which catalyzes a color producing reaction or formation of a third enzyme. Exemplary of this technique is U.S. Pat. No. 4,463,090 to Harris.

U.S. Pat. No. 4,160,645 to Ullman discloses an immunoassay procedure in which there is measured the rate of a reaction between two redox reagents. A nonenzymic catalyst for the reaction, which may include a metal ion complex, is conjugated to a ligand. When the ligand binds to an antiligand, the approach of the redox reagents to the catalyst is inhibited and the rate of the reaction is modulated.

In U.S. Pat. No. 4,375,972 to Forgione et al. and Japanese patent No. JP/20133, immunoassays involving chemiluminescent reactions catalyzed by metal ions and metalloporphyrins conjugated to a ligand are disclosed.

Catalysis of chemical reactions by metal ions is well known and provides a means for analysis of metal ions present in trace amounts. These procedures employ the metal ion to catalyze a reaction which either produces a color or degrades an existing color, and generally depend on a linear relationship between the initial rate of reaction and the concentration of metal ion.

Trace metal analysis often employs organic compounds which alone have no catalytic activity, but which can affect the catalytic activity of the metal ion and thereby either increase or decrease the rate of the reaction. Such compounds are thus modulators of metal catalysis, and may be either activators or inhibitors. Use of modulators in trace metal analysis in water is discussed by Bontchev in Talanta 19, 675 (1972). The determination of the modulators themselves is discussed by Milovanovic in Microchem. J., 28, 437 (1983) and specific examples have been described by Antonov et al. and Dolmanova et al. (J. Anal. Chem. USSR, 31, 168 (1976) and J. Anal. Chem. USSR, 32 638 (1977)).

There is a need for a method of high sensitivity to detect ligands present in biological fluids at very low levels which does not require expensive instrumentation for signal detection. It is toward the fulfillment of this need that the present invention is directed.

SUMMARY OF THE INVENTION

One aspect of the present invention is a method for detection of a ligand in a fluid. Signal means cause a detectable signal when the ligand binds to an antiligand, formation of the signal being catalyzed by a metal ion catalyst. The term catalyst is hereinafter understood to mean a metal ion catalyst. The activity of the catalyst may be modulated by a modulator actuated by an enzyme.

The fluid may be combined with an enzyme, an antiligand specific for the ligand, a blocked modulator, a substrate, and a redox reagent. Upon binding of the ligand to the antiligand, the enzyme unblocks the modulator. The free modulator thereupon modulates the catalyst, which has catalytic activity for an indicator reaction between the substrate and the redox reagent. A detectable signal indicative of the presence of the ligand in the fluid is provided by the reaction.

The catalyst may be a metal ion, preferably a transition metal ion or complex thereof, and may he either a natural or synthetic product. It may be added to the fluid or may be a metal ion endogenous in the fluid. The term metal ion is hereinafter understood to mean a free ion or a complex thereof.

The activity of the catalyst is modulated by free modulator liberated from the blocked modulator by the activated enzyme. The free modulator may be an activator or, preferably, an inhibitor. Preferred inhibitory modulators are metal binding agents which form complexes with the catalyst whereby the catalytic activity of the metal ion is inhibited. Particularly preferred inhibitory modulators are 8-hydroxyquinoline and benzyl mercaptan.

The blocked modulator is preferably the free modulator covalently conjugated with a blocking group which can subsequently be removed by the action of the enzyme. Preferred enzymes are hydrolases and preferred blocking groups are conjugated to the modulator by chemical linkages which may be cleaved by the hydrolase. The most preferred blocking groups are short peptides.

Free modulator modulates the catalyst for the indicator reaction between the substrate and the redox reagent. The indicator reaction provides a detectable signal. Preferred signals are color development or disappearance. Thus, preferred substrates are chromogens which undergo metal ion catalyzed reaction with redox reagents, such as oxidizing agents or reducing agents.

In a preferred embodiment of the invention, the enzyme is added to the fluid in an inactive form, and ligand, if present in the fluid, binds to the antiligand whereby the enzyme is activated to cleave a peptide blocking group esterified to the metal binding agent. The liberated metal binding agent complexes and thereby decreases the activity of the catalyst so that catalysis of the indicator reaction, wherein a colored chromogen is oxidized to a colorless product, is inhibited. The presence of ligand is indicated by retardation of color disappearance.

The most preferred embodiment of the invention employs the first component of complement as the enzyme, 8-hydroxyquinoline or benzyl mercaptan as the free modulator and a pentapeptide as the modulator blocking group.

The method of the invention may be heterogeneous involving a solid phase and a separation step, or it may be carried out by a homogeneous procedure which avoids the separation step.

Another aspect of the invention includes a kit of materials for performing the method of the invention substantially as described above.

Thus, the invention provides a versatile method for assay, which may be homogeneous, for ligands present in very low concentrations in a fluid. The method makes possible naked eye detection and measurement of the assay signal even though the ligand is present in concentrations as low as $10^{-12}M$. This represents signal amplification of the order of $10^6$ and greatly extends the range of ligands which can be detected or determined without expensive or cumbersome equipment. Significant savings in cost and space are thereby achieved, enabling assays in accordance with the invention to be carried out in small clinical laboratories or even in physician's offices.

DETAILED DESCRIPTION OF THE PREFERRED EMBODIMENTS

While this invention is satisfied by embodiments in many different forms, there is described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the method of the invention, a substance present in a fluid, hereinafter referred to as the ligand, may be detected visually, i.e., by naked eye observation, even when present in very low concentrations. The method includes at least two amplification stages. In one amplification stage, an indicator reaction is catalyzed by a catalyst. In a second amplification stage, the catalytic activity of the catalyst is modulated by enzymatically unblocking a modulator for the catalyst. These amplification steps take place sequentially to provide signal amplification of up to $10^6$ fold whereby a ligand present in a fluid at a level as low as $10^{-12}M$ may be detected with the naked eye. If additional amplification is desired, a first enzyme may be provided which initiates a cascade of sequential reactions involving a plurality of enzymes, any one or all of which enzymatic reactions may provide further signal amplification.

An immunological reaction is used in the method of the invention for detection of the ligand in the fluid. By the term "immunological reaction," as used herein, is meant a specific binding reaction of an antigen and an antibody, a hapten and an antibody, or any appropriate analogue of an antigen, an antibody, or a hapten which also binds specifically.

The immunological reaction may be carried out in any suitable fluid. For example, the fluid may be a body fluid suspected of containing the ligand, such as serum, urine, cerebrospinal fluid, pleural fluid or the like. Alternatively, the fluid may be water, saline or any appropriate buffer, or a mixture of body fluids and other fluids to which has been added a fluid suspected of containing ligand.

The preferred method of the invention will first be described with reference to the assay flow sheet below to provide a general understanding of the assay components and their interaction, after which each component will be discussed in detail. It is understood that, depending on the embodiment of the invention employed, the assay components may be added at the beginning of the assay procedure or at some stage during the procedure. Further, they may be added individually or in any combination, and the order in which the components are described is not to be construed as limiting the assay method to that particular order of combining the components.

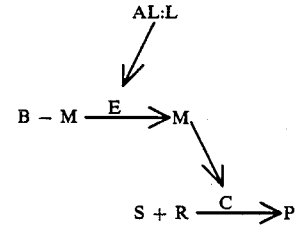

In the above flow sheet, the following definitions apply, wherein a colon indicates an immunological binding, a hyphen indicates a chemical bond or a physical attachment, such as absorption, a solid arrow indicates a chemical conversion and a dotted arrow indicates modulation of a reaction or an assay component.

E—active enzyme
AL—antiligand
L—ligand
M—modulator for catalyst

B—blocking group for modulator
C—metal ion catalyst
S—substrate
R—redox reagent
P—product It is seen from the flow sheet that active enzyme removes a blocking group from a modulator, the concentration of active enzyme being modulated by binding of ligand to antiligand and thus is proportional to the concentration of ligand in the fluid. Since unblocking of the modulator depends on the presence of active enzyme, the level of free modulator is thus also proportional to ligand concentration. Free modulator modulates (activates or inhibits) the activity of a catalyst for an indicator reaction between a substrate and a redox reagent to give a product. The level of product is either directly or inversely proportional to the level of modulator, and thus to the ligand, depending on whether the modulator is an activator or inhibitor respectively. The actual signal measured may be a color associated with the indicator reaction, as, for example, the color of the product or rate of formation thereof, or the color of the substrate or the rate of disappearance thereof, or it may be light measured as either chemiluminescence or fluorescence.

Turning now to a detailed description of the assay components, the ligand may be from any source, and may be an antigen, an antibody or a hapten. For example, the ligand may be an antigen present in a body fluid, or it may be isolated from a body fluid and subsequently introduced into a different fluid, such as buffer. In other cases, the ligand may be from a source other than a body fluid, as, for example, a culture of microorganisms or a cellular extract thereof. Preferred ligands are antigens, most preferably viral antigens present in a body fluid, such as Herpes simplex virus (HSV), Adenovirus, Influenza A virus, Parainfluenza 3 virus and Respiratory syncytial virus.

The antiligand is contacted with the ligand in the fluid to induce the immunological reaction. The antiligand may be an antigen or an antibody, either monoclonal or polyclonal, or it may be any appropriate analogue thereof which reacts specifically with the ligand. In addition, the antiligand may be an antibody complex consisting of a plurality of bound antibodies, as, for example, a second antibody bound specifically to a first antibody. Alternatively, the ligand may bind to several different antiligands, for example, an ensemble of polyclonal antibodies or a mixture of several monoclonal antibody molecules which bind simultaneously to different surface areas of the ligand. Generally, the second antibody is raised against the first antibody in a different species. The plurality of bound antibodies in the complex may contain from about two to ten or more antibodies.

The quantity of antiligand to be used may be varied over a wide range. A limited amount of antiligand having insufficient binding sites to bind all of the ligand may be used wherein the ligand binds to the antiligand in proportion to its concentration in the fluid. Preferably, excess antiligand having sufficient binding sites to bind essentially all of the ligand is used.

The fluid containing the ligand and antiligand may be incubated, if necessary, to induce binding. Incubation may be carried out at any temperature and for any length of time suitable to facilitate binding, preferably from about 20° to 40° C. for about 1 minute to 4 hours. Antiligand and ligand which are bound are hereinafter referred to as the bound fraction and antiligand and ligand which do not bind are hereinafter referred to as the free fraction. The assay may, but need not be, carried out in such a way that equilibrium is established between the bound and free fractions.

Any enzyme may be used which, in the presence of a bound fraction, can remove a blocking group from a modulator. For example, the enzyme may be conjugated to either the ligand or antiligand in any suitable way prior to the immunological reaction, and, after the reaction, the bound and free phases may be separated and the other assay components combined with the bound phase. Conjugation of the enzyme to the ligand or antiligand is conventional and well known to those skilled in the art.

In another embodiment of the invention, the enzyme is added to the assay medium under conditions whereby the enzyme is inactive until activated by a bound fraction. A suitable inactive enzyme is the first component of complement, hereinafter referred to as Cl. Cl may be added to the assay medium in any suitable form as, for example, as part of complement or any portion thereof, or it may be in serum. Preferably, Cl is separated from the other complement proteins and may, if desired, be purified prior to addition. Methods to prepare complement and isolate Cl therefrom are well known to those skilled in the art. Representative procedures are given by Medicus et al., Journal of Immunology, 125, 390 (1980).

Cl remains inactive until a complex consisting of Cl and a bound fraction is formed by a binding reaction between the Cl and the Fc portion of the antibody portion of the bound fraction. The order of binding is not important. Cl may bind to a bound fraction, or it may bind to the antibody prior to the immunological reaction. If desired, a separate incubation step may be carried out to facilitate binding of Cl to the antibody or the bound fraction. Regardless of the order of binding, formation of a complex between Cl and the bound fraction provides Cl in active form.

The modulator may be any material which modulates the activity of the catalyst and which may be maintained in inert form until actuated by the active enzyme. The modulator, when actuated, may be either an activator or an inhibitor of the catalyst and maybe used over a concentration range of $10^{-13}$ to $10^{-1}$, preferably $10^{-10}$ to $10^{-3}$M. The preferred modulator is a catalyst inhibitor which is maintained in inert form by conjugation to a group which blocks its inhibitory action until it is actuated (i.e., freed) by removal of the blocking group by the active enzyme, as described below. Preferred modulators are metal binding agents such as amino acids, wherein L-cysteine is preferred, thioureas, hydroxamates, aromatic hydroxy acids such as salicylic acid, polyamines such as ethylenediamine and ethylenediamine tetraacetic acid and most preferably thiols such as benzyl mercaptan and nitrogen heterocycles such 2,2'-dipyridyl, 1,10-phenanthroline and 8-hydroxyquinoline.

As mentioned above, a suitable enzyme is Cl, which remains inactive until activated by a hound fraction. Other suitable enzymes are hydrolases, such as, for example, proteases, esterases, phosphatases or glycosidases. The concentration of enzyme to be used depends on its activity, and may be from $10^{-6}$ to $10^{-14}$M, preferably from $10^{-9}$ to $10^{-11}$M.

Suitable blocking groups are those groups which may be conjugated to the modulator by a bond, such as an amide, thioamide, ester, or thioester bond which may be cleaved by the active enzyme. The concentration of blocked modulator may be from about $10^{-1}$ to $10^{-9}$M, preferably $10^{-3}$ to $10^{-6}$M. Thus, it is seen that the choice of blocking group depends on the enzyme used. If the enzyme is Cl, the preferred blocking group is a peptide. If the enzyme is a protease, suitable blocking groups are amino acids, carboxylic acids or peptides. If the enzyme is an esterase, suitable blocking groups are alcohols, thiols and carboxylic acids. If the enzyme is a glycosidase or a phosphatase, suitable blocking groups are carbohydrates or orthophosphate respectively. Preferred blocking groups are peptides, in particular peptides of 5 amino acid residues or less which are conjugated to the modulator by an ester bond. The most preferred blocked modulators are 8-hydroxyquinoline and benzyl mercaptan wherein the hydroxy and sulfhydryl groups are esterified with the carboxyl group of an amino acid or a peptide of 5 or fewer amino acid residues.

Enzymatic removal of the blocking group from the modulator may be carried out at any pH, preferably 6-8, which does not remove the blocking group nonenzymatically. The resulting free modulator modulates the activity of the catalyst for the indicator reaction, which may be carried out at any suitable pH, preferably 5-9. The catalyst may be endogenous in the fluid or, preferably, is added to the assay mixture in a concentration of $10^{-12}$ to $10^{-4}$, preferably $10^{-9}$ to $10^{-6}$M. Preferred catalysts are transition metal ions, such as iron, cobalt, manganese, copper, vanadium, mercury, molybdenum and silver ions or complexes of such ions. The ion complex may be a naturally occurring complex, for example, an iron porphyrin such as hemin or a cobalt porphyrin such as cobalamine. Alternatively, it may be a synthetic derivative, as, for example, a synthetic metalloporphyrin such as deuterohemin or iron (III) mesotetraarylporphine.

Some catalysts, as for example ferric ion, are of low inherent catalytic activity and may advantageously be used in the presence of a promotor of the catalytic activity. Exemplary of useful promotors are nitrogen heterocycles such as 2,2'-dipyridyl and 1,10-phenanthroline. Promotors may preferably be used in large molar excess relative to the metal ion catalyst. Thus, it is understood that a nitrogen heterocycle may, depending on the catalyst used, be either a promotor of the catalytic activity or it may be an inhibitory modulator, as described above.

The indicator reaction is the reaction of the substrate with the redox reagent in the presence of the catalyst, and results in a signal, preferably a color change. In the absence of the catalyst, the indicator reaction either does not proceed or proceeds very slowly.

Either a reducing agent or, preferably, an oxidizing agent may serve as the redox reagent, and may be used over a concentration range of $10^{-8}$ to $10^{-1}$M, preferably from $10^{-6}$ to $10^{-2}$M. Exemplary of suitable oxidizing agents are peroxides, such as hydrogen peroxide and m-chloroperbenzoic acid, bromate, chlorate, periodate, oxygen, persulfate and the like. Exemplary of suitable reducing agents are thiosulfate and ascorbic acid. The substrate may be any material which can be oxidized or reduced in the indicator reaction to give a detectable signal. Preferred substrates are aromatic amines, phenols and triarylmethanes. The most preferred substrates are chromogens having interconvertible colored and colorless forms, as, for example, alizarin red S, the violet form of which may be oxidized to a colorless form under catalysis by a metal ion, such as cobaltic ion. Other substrates may be colorless and undergo oxidation to yield a colored product or products, such as a ferric ion catalyzed oxidation of p-phenetidine. Suitable concentrations of substrate may be from $10^{-8}$ to $10^{-1}$M, preferably $10^{-6}$ to $10^{-3}$M.

The detectable signal is associated with the indicator reaction, and may be, for example, production of light. The light may be chemiluminescence, fluorescence, or it may be fluorescence detected as a result of absorption and emission of the chemiluminescence by a fluorescer. Preferably, the detectable signal is formation or disappearance of a color, or it may be a change from one color to another. In another embodiment of the invention, the signal may be a change in the rate of the indicator reaction wherein, for example, the color of a substrate is observed to remain unchanged for a specified length of time. Thus, measurements of the signal may be made under either kinetic or thermodynamic conditions. Kinetic measurements determine the rate of change which occurs over a period of time, and are generally carried out by making a series of measurements at various times after combining the assay reagents. Thermodynamic measurements determine the extent of change which has occurred when equilibrium has been reached between the substrate and the product of the indicator reaction. Measurements may be made either instrumentally or, preferably, with the naked eye.

If additional signal amplification is desired, a multistage cascade amplification assay may be carried out wherein a plurality of reagents in the assay medium react sequentially leading ultimately to modulator unblocking. In describing this embodiment of the invention, it is convenient to consider the enzyme described above as a first enzyme which enzymatically converts a reagent in the assay medium to a second enzyme which unblocks the modulator. Alternatively, the first enzyme, or any subsequent enzyme, may also react with additional reagents to provide additional enzymes which may continue the cascade of enzymatic reactions until the modulator is unblocked. By proper selection of reagents to be added to the assay medium, any desired number of amplification stages may be carried out.

It is evident that amplification occurs in any embodiment of the invention heretofore described because the enzyme, or any subsequently formed enzyme, and the metal ion catalyst act as true catalysts wherein a single molecule may act on an essentially unlimited number of blocked modulator or substrate molecules respectively without being consumed. Thus, in theory, one molecule of enzyme would be sufficient to perform the method of the invention. In practice, determination of the amounts of enzyme and catalyst to be added and the number of amplification stages to be used are well within the purview of one of ordinary skill in the art.

In another embodiment of the invention, an assay component is attached to the surface of a solid support. As known in the art, the solid support may be any support which does not substantially interfere with the assay. Exemplary of solid supports which may be used are glass and polymeric materials, such as polyethylene, polystyrene and the like. Such supports may be fabricated into any suitable shape, such as sheets, plates, wells, or preferably, tubes. For example, an assay component may be attached to the inside walls and bottom of a tube, preferably a plastic tube with one closed end. Preferably, the blocked modulator may be attached to the solid support in such a way that, when the blocking group is removed by the active enzyme, free modulator remains affixed to the solid support in proportion to the concentration of active enzyme and thus in proportion to the concentration of ligand. A wash step may then he used to remove all extraneous materials in the assay medium which might otherwise interfere with the assay, and the substrate, redox reagent and catalyst added to cause the indicator reaction.

In an alternative embodiment of the invention using a solid support, the antiligand may be attached to the solid support and incubated with ligand to bind ligand to the solid support. After a wash step to remove interfering materials, the remaining assay components may be added and the assay carried to completion as described above. If desired, this embodiment of the invention may be carried out in sandwich mode wherein ligand bound to antiligand on the solid phase may bind to a second antiligand recognizing a second determinant on the ligand. For example, the enzyme may be conjugated to the second antiligand, and the assay carried out as described above.

It is evident that an almost unlimited number of assay configurations which fall within the scope of the invention can be envisioned, including both homogeneous and heterogeneous assays carried out by either competitive or sandwich techniques. Further, the invention provides assay configurations which are suitable for either detection of the ligand or determination of its concentration. Ligand concentration may be determined by comparing the magnitude of the signal generated with the unknown with the magnitude of the signal measured upon assay of a range of known quantities of the ligand assayed under essentially identical conditions.

Another aspect of the invention is a reagent kit or package of materials for performing an assay for a ligand in accordance with the method of the invention. The kit may include an antiligand, an enzyme which may be in either active or inactive form and which may optionally be conjugated to the antiligand, and a blocked modulator for a catalyst wherein the antiligand or the blocked modulator may optionally be attached to a solid support. The kit may also include a catalyst, standards for the ligand, as, for example, one or more ligand samples of known concentration, or it may include other reagents, enzyme substrates, or other labeled or unlabeled specific antigens, antibodies or complexes thereof useful in carrying out the assay. It may include solutions, such as saline or buffers. The components of the kit may be supplied in separate containers, as, for example, vials, or two or more of the components may be combined in a single container.

The following examples are provided to further describe the invention, but are not to be construed in any way as limitative of the invention.

EXAMPLE I

In this model experiment, active Cl component Cls is used to illustrate the method of the invention. It is understood, that, in practice of the invention, interaction of a bound fraction with inactive Cl provides active subcomponent Cls.

A desalted solution of purified, activated first component of complement (Cls) containing 2.8 μg/ml protein (approximately 32 nM Cls) was prepared in pH 7.35 veronal buffered saline (VBS). One ml of a freshly prepared $2 \times 10^{-5}$ M solution of benzyl N$^2$-carbobenzyloxy-L-arginine thioester hydrochloride (blocked modulator prepared by condensation of benzylmercaptan with N$^2$-carbobenzyloxy-L-arginine hydrochloride) in VBS buffer was placed in each of a plurality of cuvettes. Buffer alone was placed in a control cuvette. To each cuvette was then added varying volumes of the complement solution, no complement being added to a second control cuvette containing thioester. The contents of the cuvettes were stirred and allowed to stand at room temperature for 10 minutes. Then to each cuvette was added 1.0 ml of a freshly prepared aqueous solution containing a mixture of 1.0 ml of 0.025% p-phenetidine hydrochloride (substrate), 3.0 ml pH 5.5 0.5M sodium acetate buffer, 1.0 ml 0.30% 2,2'-dipyridyl (promoter), and 2.5 ml H$_2$O. After stirring the resulting solutions, a freshly prepared solution of ferric chloride and potassium periodate was added to yield final concentrations of $2.1 \times 10^{-7}$M Fe (III) and $1.7 \times 10^{-4}$M oxidizing agent. The solutions were again stirred and the absorbances at 536 nm were determined at regular intervals for 10 minutes on a Beckman DU 7 Spectrophotometer, Beckman Instruments, Inc., Irvine, Calif.

The results shown in Table I indicate that there is a linear relationship between both final absorbance of the violet product and initial rate of oxidation, and the level of complement in this concentration range. The visual limit of detection of complement was approximately 250 ng (ca. 1.3 nM) and the instrumental limit was less than about $3.6 \times 10^{-10}$M.

TABLE I

| Substrate Added | Blocked Modulator Added | Complement (Cls) (ng) | Absorbance at 10 min. | Initial Rate (min$^{-1}$) |
| --- | --- | --- | --- | --- |
| + | + | 0 | 0.410 | 0.072 |
| + | + | 69 | 0.328 | 0.058 |
| + | + | 207 | 0.249 | 0.043 |
| + | + | 248 | 0.231 | 0.038 |
| + | + | 331 | 0.196 | 0.031 |
| + | − | 331 | 0.385 | 0.064 |

EXAMPLE II

This example provides a typical procedure for heterogeneous solid phase assay of HSV.

The wells of a microtiter plate are coated with specific antibody to HSV by incubating with 200 μl volumes of a solution of an antibody for the viral antigen in an appropriate buffer at 4° C. for at least 18 h. The plate is then washed with buffer. For the assay, test solutions in buffer are added in 50 μl amounts to the wells. These include a positive standard containing a known amount of antigen, negative controls without antigen, various dilutions of the sample being tested (after any necessary pretreatment), and wells to which nothing except buffer is added. After incubation at room temperature for 2 h, the wells are washed with 200 μl of buffer three times. Then 50 μl of a solution of an HSV specific antibody conjugated to Cls are added to all the wells and the plate is incubated for 2 h. Subsequently, the wells are washed five times with buffer.

To each well is then added 50 μl of a solution of benzyl N2-carbobenzyloxy-L-arginine thioester hydrochloride in buffer. After incubation for 10 to 60 min, 50 μl of freshly prepared reagent solution containing 2,2-dipyridyl and p-phenetidine hydrochloride in sodium acetate buffer (pH 5.5) in proportions similar to those in Example I are added to each well. Then a freshly prepared mixture of ferric chloride and potassium periodate is added to each well and the plate is agitated. The solutions are then incubated at room temperature for 10 min. The deepest violet color is produced in the negative controls since no inhibitor is released, while the color becomes progressively lighter with increasing amounts of antigen being present. By comparison with the positive control, a semi-quantitative determination of the level of antigen can be made by visual inspection of the colors of the sample solutions.

EXAMPLE III

This example shows the effect of various concentrations of metal binding agent on the signal produced by a color-forming indicator reaction.

Iron porphyrin deuterohemin catalyst was prepared as described in "Porphyrins and Metalloporphyrins," K.M. Smith, ed., Elsevier, 1975.

A fresh solution of 2.4 mg of catalyst in 2 ml 0.1 N NaOH was diluted with 0.01 M phosphate buffer (pH 7.4) to provide a 0.2 uM solution of the catalyst. The metal catalyst solution (1 ml) was added to various dilutions of ethanolic benzyl mercaptan in 1.0 ml of phosphate buffer containing 0.05 mM ethylenediamine tetraacetic acid in individual acrylic cuvettes and the contents stirred. Subsequently 50 µl each of solutions of the substrates N-ethyl-N-(2-hydroxy-3-sulfopropyl)-m-toluidine (87 mM) (Sigma Chemical Co.) and 4-aminoantipyrine (100mM) (Aldrich Chemical Co.) were added to each cuvette and the contents stirred. Then 25 µl of 110 mM hydrogen peroxide was added to each cuvette. After stirring once again, the absorbance at 555 nm was determined at regular intervals up to 10 min. The final absorbances obtained are given in Table II.

TABLE II

| Inhibitor Concentration (uM) | Absorbance at 10 min. |
|---|---|
| 0.0 | 0.304 |
| 1.8 | 0.208 |
| 3.6 | 0.149 |
| 5.6 | 0.135 |
| 7.4 | 0.118 |
| 9.3 | 0.100 |

It is seen that as the concentration of benzylmercaptan increases, color formation decreases because the iron porphyrin deuterohemin catalyst for the oxidation reaction is removed from the reaction mixture. This catalyst system could readily be employed for the detection of Cl or other enzymes that are capable of releasing a thiol, such as benzyl mercaptan, from a thioester blocked modulator.

In summary, the invention provides a method for detection or determination of a ligand present in a fluid at very low levels. A blocking group covalently linked to a modulator for a metal ion catalyst is removed by an enzyme. The enzyme may be conjugated to a bound fraction or it may be added to the assay medium in inactive form and subsequently activated by a bound fraction. Modulation of the catalyst by the free modulator affects the rate of an indicator reaction leading to a signal. Detection of the signal establishes the presence or absence of the ligand in the fluid. By measuring the magnitude of the signal, the concentration of the ligand may be determined. The modulator and the catalyst provide two amplification stages whereby the signal is amplified by up to $10^6$ fold, enabling naked eye detection of the signal.

What is claimed is:

1. A method for detection of a ligand in a fluid comprising:
    (a) combining a fluid suspected of containing a ligand with an antiligand specific for said ligand, an enzyme, a metal ion catalyst, a substrate, a redox reagent and an inhibitor for the activity of said catalyst wherein said inhibitor is blocked by a group coupled thereto;
    (b) causing ligand present in said fluid to bind to said antiligand to provide a bound fraction whereby said enzyme removes said blocking group thereby providing free inhibitor, said free inhibitor inhibiting the catalytic activity of said catalyst for a reaction between said substrate and said redox reagent whereby a product is formed; and
    (c) detecting said ligand by a signal associated with said reaction.

2. The method in accordance with claim 1 wherein said antiligand is attached to a solid support.

3. The method in accordance with claim 2 further comprising combining said fluid with a second antiligand specific for said ligand, said second antiligand being coupled to said enzyme.

4. The method in accordance with claim 1 wherein said enzyme is the first component of complement.

5. The method in accordance with claim 1 wherein said enzyme is a hydrolase.

6. The method in accordance with claim 5 wherein said hydrolase is selected from the group of hydrolases consisting of a protease, an esterase, a glycosidase and a phosphatase.

7. The method in accordance with claim 1 wherein said ligand is selected from the group of ligands consisting of an antigen, an antibody and a hapten.

8. The method in accordance with claim 1 wherein said antiligand is selected from the group of antiligands consisting of an antigen, an antibody and and antibody complex.

9. The method in accordance with claim 1 wherein said redox reagent is selected from the group of reagents consisting of an oxidizing agent and a reducing agent.

10. The method in accordance with claim 9 wherein said oxidizing agent is selected from the group of agents consisting of hydrogen peroxide, periodate, bromate, chlorate, persulfate, m-chloroperbenzoic acid and oxygen.

11. The method in accordance with claim 1 wherein said free inhibitor is a metal binding agent.

12. The method in accordance with claim 11 wherein said metal binding agent is selected from the group of agents consisting of an amino acid, a thiol, a thiourea, a nitrogen heterocycle, a hydroxamate, a polyamine and a hydroxy acid.

13. The method in accordance with claim 12 wherein said metal binding agent is selected from the group of agents consisting of 8-hydroxyquinoline, benzylmercaptan, L-cysteine, ethylenediamine, salicylic acid and ethylenediamine tetraacetic acid.

14. The method in accordance with claim 1 wherein said blocking group is selected from the group of blocking groups consisting of a peptide, an amino acid, a carboxylic and, an alcohol, a carbohydrate and an orthophosphate.

15. The method in accordance with claim 1 wherein said catalyst is selected from the group of catalysts consisting of a metal ion and a metal ion complex.

16. The method in accordance with claim 15 wherein said metal ion is selected from the group of ions consisting of an ion of iron, cobalt, manganese, copper, vanadium, mercury, molybdenum and silver.

17. The method in accordance with claim 15 wherein said metal ion complex is selected from the group of complexes consisting of hemin, cobalamine, deuterohemin and iron (III) meso-tetraphenylporphine.

18. The method in accordance with claim 1 wherein said substrate is selected from the group of substrates consisting of aromatic amines, phenols and triarylmethanes.

19. The method in accordance with claim 1 wherein said signal is a color associated with said substrate.

20. The method in accordance with claim 1 wherein said signal is a color associated with said product.

21. The method in accordance with claim 1 wherein said signal is light associated with said product.

22. The method in accordance with claim 21 wherein said light is chemiluminescence.

23. The method in accordance with claim 21 wherein said light is fluorescence.

24. The method in accordance with claim 1 wherein an incubation causes step (b).

25. The method in accordance with claim 1 wherein said blocked inhibitor is attached to a solid support.

26. The method in accordance with claim 25 further comprising separating the fluid phase of said mixture from said solid support.

27. The method in accordance with claim 1 further comprising combining said fluid with a promotor for said catalytic activity.

28. The method in accordance with claim 27 wherein said promotor is selected from the group consisting of 2,2'-dipyridyl and 1,10-phenanthroline.

29. A method for detection of a ligand in a fluid comprising:
(a) combining a fluid suspected of containing a ligand with the first component of complement, an antiligand specific for said ligand, a metal ion catalyst, an oxidizing agent, a substrate for said oxidizing agent, and a metal ion binding agent said binding agent being coupled to a peptide which blocks its binding properties;
(b) causing ligand present in said fluid to bind to said antiligand, said binding activating said first component of complement, said activated first component of complement removing said peptide thereby providing free binding agent which binds said metal ion catalyst whereby the catalytic activity of said catalyst for a reaction between said substrate and said oxidizing agent is reduced; and
(c) detecting said ligand by inhibition of a color change associated with said reaction.

30. The method in accordance with claim 29 wherein said metal binding agent coupled to said peptide is benzyl $N^2$-carbobenzyloxy-L-arginine thioester hydrochloride.

31. A method for detection of a ligand in a fluid comprising:
(a) combining a fluid suspected of containing a ligand with a first antiligand specific for said ligand attached to a solid support and a second antiligand having coupled thereto a hydrolase;
(b) causing ligand present in said fluid to bind to said first and second antiligands to give a bound phase and a free phase;
(c) separating said bound phase from said free phase;
(d) contacting said bound phase with an oxidizing agent, a substrate for said oxidizing agent, a metal ion catalyst and a metal ion binding agent, said metal ion binding agent being coupled to a blocking group which blocks its binding properties, wherein said hydrolase removes said blocking group thereby providing free binding agent which binds said metal ion catalyst, thereby inhibiting the catalytic activity of said catalyst for a reaction between said substrate and said oxidizing agent; and
(e) detecting said ligand by inhibition of a color change associated with said reaction.

32. A method for determination of the concentration of a ligand in a fluid comprising:
(a) combining the first component of complement, a substrate, a redox reagent, a metal ion catalyst, an inert inhibitor for said catalyst, a fluid containing an unknown quantity of a ligand and an antiligand for said ligand;
(b) causing said antiligand to bind to said ligand, said binding enabling said first component of complement to actuate said inert inhibitor, said actuated inhibitor inhibiting the catalytic activity of said catalyst for a reaction between said substrate and said redox reagent;
(c) measuring a signal associated with said reaction; and
(d) comparing the magnitude of said signal with the magnitude of a signal associated with said reaction when steps (a) to (c) are repeated with fluid samples containing known quantities of said ligand.

33. A kit of materials for performing an assay for a ligand in a fluid comprising an antiligand for a ligand, an enzyme and a blocked inhibitor for a metal catalyst.

34. The kit in accordance with claim 33 wherein said enzyme is conjugated to said antiligand.

35. The kit in accordance with claim 33 wherein at least one of said blocked inhibitor and said antiligand is attached to a solid support.

36. The kit in accordance with claim 33 further comprising at least one fluid sample containing ligand of known concentration.

37. The kit in accordance with claim 33 further comprising a fluid sample substantially free of ligand.

38. The kit in accordance with claim 33 further comprising at least one other reagent selected from the group of reagents consisting of substrates, metal ion catalysts, redox reagents, antigens, antibodies and complexes thereof, buffers and saline.

39. The kit in accordance with claim 33 further comprising one or more containers.

* * * * *